(12) United States Patent
Gaudin

(10) Patent No.: US 7,767,639 B2
(45) Date of Patent: Aug. 3, 2010

(54) UNSATURATED ETHERS AS PERFUMING INGREDIENTS

(75) Inventor: Jean-Marc Gaudin, Annemasse (FR)

(73) Assignee: Firmenich SA, Geneva (CH)

( * ) Notice: Subject to any disclaimer, the term of this patent is extended or adjusted under 35 U.S.C. 154(b) by 828 days.

(21) Appl. No.: 11/611,076

(22) Filed: Dec. 14, 2006

(65) Prior Publication Data

US 2007/0087956 A1  Apr. 19, 2007

Related U.S. Application Data

(63) Continuation of application No. PCT/IB2005/002465, filed on Aug. 22, 2005.

(30) Foreign Application Priority Data

Aug. 27, 2004  (WO) ................ PCT/IB2004/002778

(51) Int. Cl.
*A61K 8/18* (2006.01)
*A61K 8/00* (2006.01)

(52) U.S. Cl. ............................ 512/25; 512/1; 424/401; 510/119

(58) Field of Classification Search ................ 512/1, 512/25
See application file for complete search history.

(56) References Cited

U.S. PATENT DOCUMENTS

| | | | |
|---|---|---|---|
| 3,248,430 A | 4/1966 | Kimel | 260/615 |
| 3,786,075 A * | 1/1974 | Teisseire et al. | 568/665 |
| 4,031,141 A | 6/1977 | Hoffmann et al. | 260/614 R |
| 5,538,943 A | 7/1996 | Naef et al. | 512/1 |

FOREIGN PATENT DOCUMENTS

EP  0 694 604 B1  1/1996

OTHER PUBLICATIONS

B. Genevieve et al., XP-002366425, "Vinylallenes IX, Preparation of Some 1,2,4,6-Tetraenes" Tetrahedron Letters, No. 1 pp. 7-10 (1979).

* cited by examiner

*Primary Examiner*—James Seidleck
*Assistant Examiner*—Saira Haider
(74) *Attorney, Agent, or Firm*—Winston & Strawn LLP

(57) ABSTRACT

The present invention concerns a compound of formula

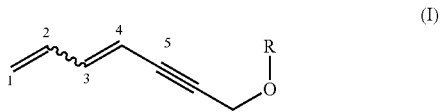

wherein the wavy line indicates that the double bond in position 3 is in a configuration E or Z or a mixture thereof, and R is a $C_2$-$C_6$ alkyl or alkenyl group, which is a useful perfuming ingredient capable of imparting odor notes of the violet leaves type as well as a green/fruity aspect.

10 Claims, No Drawings

UNSATURATED ETHERS AS PERFUMING INGREDIENTS

CROSS-REFERENCE TO RELATED APPLICATIONS

This application is a continuation of International application PCT/IB2005/002465 filed on Aug. 22, 2005, the entire content of which is expressly incorporated herein by reference thereto.

TECHNICAL FIELD

The present invention relates to a compound of formula

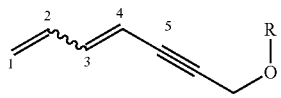

wherein the wavy line indicates that the double bond in position 3 has a configuration E or Z or a mixture thereof, and R is a $C_2$-$C_6$ alkyl or alkenyl group, which is a useful perfuming ingredient.

BACKGROUND

To the best of our knowledge, the invention's compounds are novel.

The closest known analogue is 7-methoxy-1,3-heptadien-5-yne, which is reported as a chemical intermediate in *Tetrahedron Letters,* 1979, 1, pg 7-10. In the document there is no mention or suggestion of any odor properties of the invention's compounds.

Amongst the known compounds having similar odor properties it is useful to mention 1,3-undecadien-5-yne disclosed in EP 694604. However in the document there is no suggestion that an oxa-analogue according to the invention may have an odor at all and even less an odor useful in perfumery.

SUMMARY OF THE INVENTION

The present invention now relates compound of formula

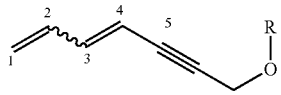

as defined herein below. Other aspects of the present invention concern the use of this compound (I) in the perfumery industry as well as the compositions or articles associated with this compound.

DETAILED DESCRIPTION OF THE PREFERRED EMBODIMENTS

We have now surprisingly discovered that the compound of formula

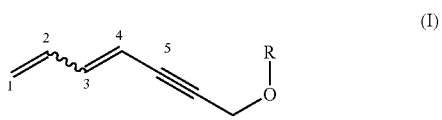

wherein the wavy line indicates that the double bond in position 3 has a configuration E or Z or a mixture thereof, and R is a linear, branched or cyclic $C_2$-$C_6$ alkyl or alkenyl group; is a useful perfuming ingredient which imparts odor notes of the violet leaves type as well as a green/fruity aspect.

According to a particular embodiment of the invention, R represents a $C_2$-$C_4$ alkyl group, and in particular a propyl group.

According to a further embodiment the invention's compounds can be in the form of a mixture of isomers of configuration (3E) or (3Z) and in which the isomer of configuration (3E) represents at least 60% by weight, relative to the weight of the mixture.

Amongst the compounds of formula (I), one may cite in particular, and as non-limiting example, 7-propoxy-1,3-heptadien-5-yne which possesses an odor reminding the one of methyl octin carbonate or of 1,3-undecadien-5-yne. However the odor of the invention's compound differs from the one of the prior art compounds by a more pronounced violet-leaves and an amylic character and a fruity note which is more in the direction of mango. Furthermore, the fresh and fruity aspect of the present invention renders its use more flexible than the one of the prior art compounds mentioned above.

Other examples of invention compound are 7-(pentyloxy)-1,3-heptadien-5-yne or 7-(allyloxy)-1,3-heptadien-5-yne which have also an odor reminding of the one of methyl octin carbonate or of 1,3-undecadien-5-yne.

As mentioned above, the invention concerns the use of a compound of formula (I) as perfuming ingredient. In other words it concerns a method to confer, enhance, improve or modify the odor properties of a perfuming composition or of a perfumed article, which method comprises adding to the composition or article an effective amount of at least a compound of formula (I). By "use of a compound of formula (I)" it has to be understood here also the use of any composition containing the compound (I) and which can be advantageously employed in perfumery industry as active ingredients.

The compositions, which are in fact perfuming compositions that can be advantageously employed as perfuming ingredient, are also an object of the present invention.

Therefore, the present invention also relates to a perfuming composition comprising:

i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. The carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials, for examples, may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

Generally speaking, by "perfumery base" we mean here a composition comprising at least one perfuming co-ingredient.

The perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and the perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that the co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that the ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords possessing the odor tonality of various compounds of the invention, creating thus new tools for their work.

Furthermore, the invention's compound can also be advantageously used in all the fields of modem perfumery to positively impart or modify the odor of a consumer product into which the compound (I) is added. Consequently, a perfumed article comprising:

i) as perfuming ingredient, at least one compound of formula (I); and ii) a consumer product base, is also an object of the present invention.

For the sake of clarity, it has to be mentioned that, by "consumer product base" we mean here a consumer product which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of the product.

Examples of suitable consumer products include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or anti-perspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 5% by weight, or even more, of the compounds of the invention based on the weight of the composition into which they are incorporated. Concentrations lower than these, such as in the order of 0.01% to 1% by weight, can be used when these compounds are incorporated into perfumed articles.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ with a 360 or 400 MHz machine for $^1$H and $^{13}$C, the chemical displacements δ are indicated in ppm with respect to TMS as standard, the coupling constants J are expressed in Hz.

Example 1

Synthesis of Compounds of Formula (I)

A) Preparation of the Precursor: General Procedure

A 500 ml three necked flask was charged with 100 mmoles of a solution of isopropyl magnesium chloride 2M in Et$_2$O (origin: Fluka). Then 100 mmoles of the starting alkyne was added over a period of 30 minutes while maintaining the temperature around 30° C. The reaction was left at room temperature for 1 hour and 100 mmoles of crotonaldehyde diluted in 100 ml of dry Et$_2$O was added over a period of 20 minutes. After an additional period of 30 minutes, the reaction mixture was poured into cold water (200 ml) containing 10 ml of acetic acid. The organic phase was washed with water and the solvent removed under vacuum. The crude product was rapidly distilled under reduced pressure (Kugelrohr distillation) to provide the desired precursor.

i) (2E)-7-(Allyloxy)-2-hepten-5-yn-4-ol

Starting alkyne: 3-prop-2-ynyloxy-propene Yields=60%

MS m/z: 148 (1), 135 (4), 121 (13), 109 (12), 107 (13), 95 (28), 91 (26), 79 (60), 77 (42), 69 (25), 67 (25), 65 (23), 55 (37), 53 (38), 43 (30), 41 (100), 39 (72).

$^{13}$C-NMR: 17.46 (q), 57.39 (t), 62.73 (d), 70.64 (t), 81.53 (s), 86.06 (s), 117.98 (t), 128.7 (d), 130.11 (d), 133.89 (d).

$^1$H-NMR: 1.72 (3H, t, J=7 Hz); 2.77 (1H, OH); 4.07 (2H, d, J=7 Hz); 4.21 (2H, d, J=1 Hz); 4.86 (1H, d, J=7 Hz); 5.22 (1H, d, J=10 Hz); 5.31 (1H, d, J=17 Hz); 5.61 (1H, dd, J$_d$=15 Hz, J$_d$=7 Hz); 5.89 (2H, m).

ii) (2E)-7-Propoxy-2-hepten-5-yn-4-ol

Starting alkyne: 3-propoxy-1-prop-2-yne Yields=89%

MS m/z: 153 (3), 139 (9), 111 (20), 109 (15), 97 (22), 95 (36), 91 (20), 81 (36), 79 (100), 77 (34), 66 (52), 43 (77), 41 (79).

$^{13}$C-NMR: 10.54 (q), 17.46 (q), 22.69 (t), 58.24 (t), 62.73 (d), 71.90 (t), 81.89 (s), 85.73 (s), 128.63 (d), 130.21 (d).

$^1$H-NMR: 0.92 (3H, t, J=7 Hz); 1.60 (2H, m); 1.72 (3H, d, J=7 Hz); 3.47 (2H, J=7 Hz); 4.19 (2H, d, J=1 Hz); 4.86 (1H, d, J=7 Hz); 5.62 (1H, dd, J$_d$=16 Hz, J$_d$=7 Hz); 5.87 (1H, dq, J$_d$=16 Hz, J$_q$=7 Hz).

iii) (2E)-7-(Pentyloxy)-2-hepten-5-yn-4-ol

Starting alkyne: 3-pentyloxy-1-prop-2-yne Yields=90%

MS m/z: 196 (1, M$^+$), 181 (2), 178 (1), 167 (2), 139 (23), 126 (16), 111 (32), 108 (27), 95 (45), 79 (100), 69 (40), 66 (44), 43 (16).

$^{13}$C-NMR: 14.02 (q), 17.46 (q), 22.50 (t), 28.27 (t), 29.17 (t), 58.27 (t), 62.76 (d), 70.30 (t), 81.95 (s), 85.70 (s), 128.66 (d), 130.20 (d).

$^1$H-NMR: 0.90 (3H, t, J=7 Hz); 1.33 (4H, m); 1.60 (2H, m); 1.72 (3H, d, J=7 Hz); 2.70 (1H, OH); 3.50 (2H, t, J=7 Hz); 4.19 (2H, d, J=1 Hz); 4.85 (1H, d, J=7 Hz); 5.62 (1H, dd, J$_d$=16 Hz, J$_d$=7 Hz); 5.88 (1H, dq, J$_d$=16 Hz, J$_q$=7 Hz).

B) Conversion of the Precursor Into the Invention Compound: General Procedure

A 500 ml three necked flask was charged with 50 mmoles of a solution of precursor obtained above in 300 ml of toluene and 0.5 g of para-toluenesulfonic acid monohydrate. The reaction was heated at reflux with a Dean-Stark apparatus to remove the water formed. After 30 minutes the reaction was cooled at room temperature and washed three times with water. The solvent was removed under vacuum and the crude invention product was purified by bulb-to-bulb distillation.

The invention product was obtained in the form of a 85/15 mixture of isomers of configuration (3E) or (3Z).

i) 7-(Allyloxy)-1,3-heptadien-5-yne

Starting precursor: (2E)-7-(allyloxy)-2-hepten-5-yn-4-ol Yields=62%

Isomer (3E):

$^{13}$C-NMR: 57.93 (t), 70.60 (t), 85.18 (s), 87.85 (s), 111.28 (d), 117.79 (t), 119.96 (t), 134.06 (d), 136.02 (d), 142.62 (d).

$^1$H-NMR: 4.07 (2H, d, J=7 Hz); 4.29 (2H, d, J=1 Hz); 5.20 (2H, m); 5.30 (2H, m); 5.64 (1H, d, J=17 Hz); 5.91 (1H, m); 6.36 (1H, m); 6.59 (1H, m).

Isomer (3Z):

$^{13}$C-NMR: 57.83 (t), 70.60 (t), 83.09 (s), 91.41 (s), 108.37 (d), 109.27 (t), 120.60 (t), 133.93 (d), 140.83 (d), 147.39 (d).

ii) 7-(Propoxy)-1,3-heptadien-5-yne

Starting precursor: (2E)-7-Propoxy-2-hepten-5-yn-4-ol Yields=43%

Isomer (3E):

$^{13}$C-NMR: 10.57 (q), 22.81 (t), 58.80 (t), 71.88 (t), 84.83 (s), 88.30 (s), 111.40 (d), 119.8 (t), 136.07 (d), 142.50 (d).

$^1$H-NMR: 0.94 (3H, t, J=7 Hz); 1.62 (2H, m); 3.47 (2H, t, J=7 Hz); 4.27 (2H, d, J=1 Hz); 5.19 (1H, d, J=11 Hz); 5.30 (1H, d, J=16 Hz); 5.65 (1H, d, J=15 Hz); 6.36 (1H, dt, J$_d$=16 Hz, J$_t$=11 Hz); 6.58 (1H, dd, J$_d$=15 Hz, J$_d$=11 Hz).

Isomer (3Z):

$^{13}$C-NMR: 10.57 (q), 22.81 (t), 58.80 (t), 71.88 (t), 82.75 (s), 91.85 (s), 109.39 (d), 120.47 (t), 133.98 (d), 140.69 (d).

$^1$H-NMR: 0.94 (3H, t, J=7 Hz); 1.62 (2H, m); 3.47 (2H, t, J=7 Hz); 4.31 (2H, d, J=1 Hz); 5.28 (1H, d, J=11 Hz); 5.37 (1H, d, J=16 Hz); 5.50 (1H, d, J=11 Hz); 6.39 (1H, d, J=11 Hz); 6.86 (1H, dt, J$_d$=16 Hz, J$_t$=11 Hz).

iii) 7-(Pentyloxy)-1,3-heptadien-5-yne

Starting precursor: (2E)-7-(Pentyloxy)-2-hepten-5-yn-4-ol Yields=20%

Isomer (3E):

$^{13}$C-NMR: 14.04 (q), 22.53 (t), 28.32 (t), 29.29 (t), 58.82 (t), 70.24 (t), 84.83 (s), 88.31 (s), 111.40 (d), 119.82 (t), 136.07 (d), 142.48 (d).

$^1$H-NMR: 0.90 (3H, t, J=7 Hz); 1.33 (4H, m); 1.60 (2H, m); 3.52 (2H, t, J=7 Hz); 4.24 (2H, d, J=1 Hz); 5.18 (1H, d, J=11 Hz); 5.30 (1H, d, J=16 Hz); 5.64 (1H, d, J=15 Hz); 6.36 (1H, dt, J$_d$=16 Hz, J$_t$=11 Hz); 6.58 (1H, dd, J$_d$=15 Hz, J=11 Hz).

Isomer (3Z):

$^{13}$C-NMR : 14.04 (q), 22.53 (t), 28.32 (t), 29.29 (t), 58.82 (t), 70.28 (t), 82.75 (s), 91.87 (s), 109.40 (d), 120.44 (t), 133.33 (d), 140.67 (d).

Example 2

Preparation of a Perfuming Composition

A perfuming composition of the "fruity-green-musk" type was prepared by admixing the following ingredients:

| Ingredient | Parts by weight |
| --- | --- |
| 10%* Ethyl 2-methyl-pentanoate[1] | 65 |
| Benzylacetone | 20 |
| Allyl caproate | 10 |
| Allyl cyclohexylpropionate | 15 |
| Cis-2-pentyl-1-cyclopentanol[1] | 5 |
| 10%* Delta Damascone | 45 |
| 3-Methylbutyl 2-phenylethyl ether | 10 |
| 10%* 2,4,6-Trimethyl-4-phenyl-1,3-dioxane | 30 |
| HABANOLIDE ®[2] | 20 |
| HEDIONE ®[3] | 15 |
| Isojasmone | 5 |
| 1%* 2,6-Dimethyl-5-heptanal | 20 |
| 2,4-Dimethyl-3-cyclohexen-1-carboxaldehyde | 5 |
| 4-Undecanolide | 15 |
| VERDOX ®[4] | 100 |
| | 380 |

*in dipropyleneglycol
[1]Origin: Firmenich SA, Geneva, Switzerland
[2]Pentadecenolide; origin: Firmenich SA, Geneva, Switzerland
[3]3-(4-Tert-butylphenyl)-2-methylpropanal; origin: Givaudan-Roure SA, Vernier, Switzerland
[4]2-tert-butyl-1-cyclohexyl acetate; origin: International Flavors & Fragrances, USA The addition of 2 parts by weight of 7-(Propoxy)-1,3-heptadien-5-yne to the above-described perfuming composition imparted to the fragrance of the latter a freshness and a fruity note, of the mango type. The addition of the same amount of 1,3-undecadien-5-yne imparted a note more violet, less fruity and an overall effect less balanced and warm.

What is claimed is:

1. A compound of formula

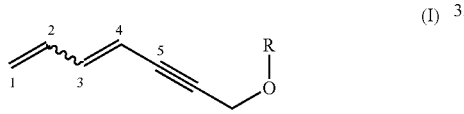

wherein the wavy line indicates that the double bond in position 3 has a configuration E or Z or a mixture thereof, and R is an n-propyl group.

2. A compound according to claim 1, wherein the compound is in the form of a mixture of isomers of configuration (3E) or (3Z) and in which the isomer of configuration (3E) represents at least 60% by weight, relative to the weight of the mixture.

3. A perfuming composition comprising
   i) at least one compound as defined in claim 1;
   ii) at least one ingredient selected from the group consisting of a perfumery carrier and a perfumery base; and
   iii) optionally at least one perfumery adjuvant.

4. A method to confer, enhance, improve or modify the odor properties of a perfuming composition or of a perfumed article, which method comprises adding to the composition or article an effective amount of at least a compound as defined in claim 1.

5. A perfumed article comprising:
   i) at least one compound as defined in claim 1; and
   ii) a consumer product base.

6. A perfumed article according to claim 5, wherein the non-palatable consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

7. A perfuming composition comprising
   i) at least one compound of formula (I):

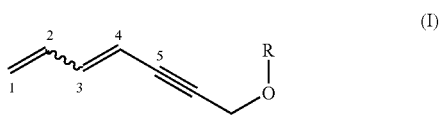

wherein the wavy line indicates that the double bond in position 3 has a configuration E or Z or a mixture thereof, and R is a linear, branched or cyclic $C_2$-$C_6$ alkyl or alkenyl group;
   ii) at least one ingredient selected from the group consisting of a perfumery carrier and a perfumery base; and
   iii) optionally at least one perfumery adjuvant.

8. A method to confer, enhance, improve or modify the odor properties of a perfuming composition or of a perfumed article, which method comprises adding to the composition or article an effective amount of at least a compound of formula (I):

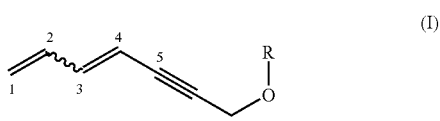

wherein the wavy line indicates that the double bond in position 3 has a configuration E or Z or a mixture thereof, and R is a linear, branched or cyclic $C_2$-$C_6$ alkyl or alkenyl group.

9. A perfumed article comprising:
   i) at least one compound of formula (I) of formula (I):

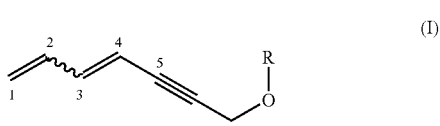

wherein the wavy line indicates that the double bond in position 3 has a configuration E or Z or a mixture thereof, and R is a linear, branched or cyclic $C_2$-$C_6$ alkyl or alkenyl group; and
   ii) a consumer product base.

10. A perfumed article according to claim 9, wherein the non-palatable consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

* * * * *